(12) United States Patent
Wellons et al.

(10) Patent No.: US 9,330,133 B2
(45) Date of Patent: *May 3, 2016

(54) VIRTUAL PHYSICIAN OFFICE SYSTEMS AND METHODS

(71) Applicant: AT&T Intellectual Property I, L.P., Atlanta, GA (US)

(72) Inventors: David L Wellons, Marietta, GA (US); Diane Brown Turcan, Smyrna, GA (US)

(73) Assignee: AT&T INTELLECTUAL PROPERTY I, L.P., Atlanta, GA (US)

( * ) Notice: Subject to any disclaimer, the term of this patent is extended or adjusted under 35 U.S.C. 154(b) by 82 days.

This patent is subject to a terminal disclaimer.

(21) Appl. No.: 14/228,332

(22) Filed: Mar. 28, 2014

(65) Prior Publication Data
US 2014/0214876 A1    Jul. 31, 2014

Related U.S. Application Data

(63) Continuation of application No. 11/805,104, filed on May 22, 2007, now Pat. No. 8,712,031, which is a continuation of application No. 10/351,801, filed on Jan. 27, 2003, now Pat. No. 7,248,688.

(51) Int. Cl.
| | |
|---|---|
| *H04M 5/00* | (2006.01) |
| *G06F 17/30* | (2006.01) |
| *G06Q 10/10* | (2012.01) |
| *G06Q 50/22* | (2012.01) |
| *G06Q 50/26* | (2012.01) |
| *H04L 29/06* | (2006.01) |
| *H04L 29/08* | (2006.01) |

(52) U.S. Cl.
CPC .......... *G06F 17/30386* (2013.01); *G06Q 10/10* (2013.01); *G06Q 50/22* (2013.01); *G06Q 50/265* (2013.01); *H04L 29/06* (2013.01); *H04L 67/10* (2013.01); *H04L 67/12* (2013.01); *H04L 67/14* (2013.01); *H04L 69/329* (2013.01)

(58) Field of Classification Search
CPC .............. H04M 3/5191; H04M 3/5232; G06F 17/30386
USPC .............. 379/265.01–265.14, 266.01–266.1, 379/309, 219, 220.01, 221.01
See application file for complete search history.

(56) References Cited

U.S. PATENT DOCUMENTS

| | | |
|---|---|---|
| 4,817,130 A | 3/1989 | Frimmel, Jr. |
| 4,979,206 A | 12/1990 | Padden et al. |
| 5,062,103 A | 10/1991 | Davidson et al. |

(Continued)

OTHER PUBLICATIONS

NEC, Fusion Certification Announcement, Oct. 24, 2000, 3 pages.

*Primary Examiner* — William Deane, Jr.
(74) *Attorney, Agent, or Firm* — Scott P. Zimmerman, PLLC

(57) ABSTRACT

Electronic records are formatted according to recipient addresses. When an electronic database record is received by a server or other device, the electronic database record has any formatting, herein termed a legacy format. The electronic database record is destined for delivery to device identified by a recipient address. The recipient address is associated with a software agent that reformats the legacy format into a different format. The electronic database record is thus reformatted according to software agent associated with the recipient address. A reformatted database record is thus sent to the recipient address, and the reformatted database record has the different format.

20 Claims, 11 Drawing Sheets

(56) References Cited

U.S. PATENT DOCUMENTS

| | | |
|---|---|---|
| 5,062,133 A | 10/1991 | Melrose |
| 5,113,429 A | 5/1992 | Morley, Jr. et al. |
| 5,278,955 A | 1/1994 | Forte et al. |
| 5,283,856 A | 2/1994 | Gross et al. |
| 5,418,628 A | 5/1995 | Perkins |
| 5,559,855 A | 9/1996 | Dowens et al. |
| 5,619,991 A | 4/1997 | Sloane |
| 5,651,058 A | 7/1997 | Hackett-Jones et al. |
| 5,678,179 A | 10/1997 | Turcotte et al. |
| 5,711,297 A | 1/1998 | Iliff |
| 5,748,100 A | 5/1998 | Gutman et al. |
| 5,764,731 A | 6/1998 | Yablon |
| 5,815,566 A | 9/1998 | Ramot et al. |
| 5,822,418 A | 10/1998 | Yacenda et al. |
| 5,841,854 A | 11/1998 | Schumacher et al. |
| 5,867,821 A | 2/1999 | Ballantyne et al. |
| 5,868,669 A | 2/1999 | Iliff |
| 5,872,841 A | 2/1999 | King et al. |
| 5,878,130 A | 3/1999 | Andrews et al. |
| 5,915,010 A | 6/1999 | McCalmont |
| 5,917,893 A | 6/1999 | Katz |
| 5,924,074 A | 7/1999 | Evans |
| 5,930,759 A | 7/1999 | Moore et al. |
| 5,940,740 A | 8/1999 | Aas et al. |
| 5,946,659 A | 8/1999 | Lancelot et al. |
| 5,951,645 A | 9/1999 | Goto |
| 5,963,864 A | 10/1999 | O'Neil |
| 6,006,206 A | 12/1999 | Smith et al. |
| 6,009,432 A * | 12/1999 | Tarin |
| 6,018,713 A | 1/2000 | Coli et al. |
| 6,035,021 A | 3/2000 | Katz |
| 6,052,442 A | 4/2000 | Cooper et al. |
| 6,075,787 A | 6/2000 | Bobeck et al. |
| 6,088,429 A | 7/2000 | Garcia |
| 6,088,677 A | 7/2000 | Spergeon |
| 6,112,183 A | 8/2000 | Swanson et al. |
| 6,119,108 A | 9/2000 | Holmes et al. |
| 6,122,485 A | 9/2000 | Archer |
| 6,125,176 A | 9/2000 | Foladare et al. |
| 6,137,524 A | 10/2000 | Chea |
| 6,137,876 A | 10/2000 | Wong et al. |
| 6,151,586 A | 11/2000 | Brown |
| 6,185,603 B1 | 2/2001 | Henderson et al. |
| 6,201,804 B1 | 3/2001 | Kikinis |
| 6,206,829 B1 | 3/2001 | Iliff |
| 6,229,888 B1 | 5/2001 | Miloslavsky |
| 6,272,319 B1 | 8/2001 | Narusawa |
| 6,282,565 B1 | 8/2001 | Shaw et al. |
| 6,295,551 B1 | 9/2001 | Roberts et al. |
| 6,305,007 B1 | 10/2001 | Mintz |
| 6,310,543 B1 | 10/2001 | Yoshioka et al. |
| 6,324,279 B1 | 11/2001 | Kalmanek et al. |
| 6,339,593 B1 | 1/2002 | Kikinis |
| 6,366,658 B1 | 4/2002 | Bjornberg et al. |
| 6,373,817 B1 | 4/2002 | Kung et al. |
| 6,373,871 B1 | 4/2002 | Hemmes et al. |
| 6,374,229 B1 | 4/2002 | Lowrey et al. |
| 6,408,068 B1 | 6/2002 | Larson et al. |
| 6,411,947 B1 | 6/2002 | Rice et al. |
| 6,434,121 B1 | 8/2002 | Davidson et al. |
| 6,445,784 B2 | 9/2002 | Uppaluru et al. |
| 6,456,594 B1 | 9/2002 | Kaplan et al. |
| 6,462,656 B2 | 10/2002 | Ulrich et al. |
| 6,473,404 B1 | 10/2002 | Kaplan et al. |
| 6,482,156 B2 | 11/2002 | Iliff |
| 6,496,878 B1 * | 12/2002 | Azevedo et al. ............ 710/22 |
| 6,501,562 B1 | 12/2002 | Nakagiri et al. |
| 6,532,489 B1 | 3/2003 | Merchant |
| 6,539,393 B1 | 3/2003 | Kabala |
| 6,561,809 B1 | 5/2003 | Lynch et al. |
| 6,594,354 B1 | 7/2003 | Kelly |
| 6,603,847 B1 | 8/2003 | Griffith |
| 6,611,590 B1 | 8/2003 | Lu et al. |
| 6,631,271 B1 | 10/2003 | Logan |
| 6,633,848 B1 | 10/2003 | Johnson et al. |
| 6,674,403 B2 | 1/2004 | Gray et al. |
| 6,680,999 B1 | 1/2004 | Garcia |
| 6,721,412 B1 | 4/2004 | Youngs |
| 6,727,818 B1 | 4/2004 | Wildman et al. |
| 6,771,173 B1 | 8/2004 | Clayton et al. |
| 6,785,380 B2 | 8/2004 | Ribera |
| 6,810,429 B1 | 10/2004 | Walsh et al. |
| 6,859,649 B1 | 2/2005 | Denenberg et al. |
| 6,888,927 B1 | 5/2005 | Cruickshank et al. |
| 6,892,083 B2 | 5/2005 | Shostak |
| 6,898,625 B2 | 5/2005 | Henry et al. |
| 6,970,548 B2 | 11/2005 | Pines et al. |
| 6,996,406 B2 | 2/2006 | Lection et al. |
| 7,023,979 B1 | 4/2006 | Wu et al. |
| 7,136,475 B1 | 11/2006 | Rogers et al. |
| 7,167,553 B2 | 1/2007 | Shaffer et al. |
| 7,191,221 B2 | 3/2007 | Schatz et al. |
| 7,248,688 B2 | 7/2007 | Wellons et al. |
| 7,327,756 B2 | 2/2008 | Hamlin |
| 7,376,470 B2 | 5/2008 | Tanaka |
| 7,376,704 B2 | 5/2008 | Wellons et al. |
| 7,644,169 B2 * | 1/2010 | Cleghorn et al. ............ 709/230 |
| 7,672,003 B2 | 3/2010 | Dowling et al. |
| 7,782,907 B2 | 8/2010 | Agrawal |
| 8,326,651 B2 | 12/2012 | McLaren et al. |
| 2002/0004727 A1 | 1/2002 | Knaus et al. |
| 2002/0010679 A1 | 1/2002 | Felsher |
| 2002/0016818 A1 | 2/2002 | Kirani et al. |
| 2002/0049615 A1 | 4/2002 | Huber |
| 2002/0055917 A1 | 5/2002 | Muraca |
| 2002/0055967 A1 | 5/2002 | Coussement |
| 2002/0065758 A1 | 5/2002 | Henley |
| 2002/0068575 A1 | 6/2002 | Agrawal et al. |
| 2002/0076026 A1 | 6/2002 | Batten |
| 2002/0080416 A1 | 6/2002 | Quine |
| 2002/0106071 A1 | 8/2002 | Uppaluru et al. |
| 2002/0112008 A1 | 8/2002 | Christenson et al. |
| 2002/0114278 A1 | 8/2002 | Coussement |
| 2002/0120687 A1 | 8/2002 | Diacakis et al. |
| 2002/0143876 A1 | 10/2002 | Boyer et al. |
| 2002/0144154 A1 | 10/2002 | Tomkow |
| 2002/0163572 A1 | 11/2002 | Center, Jr. et al. |
| 2002/0167935 A1 | 11/2002 | Nabkel et al. |
| 2002/0188689 A1 | 12/2002 | Michael |
| 2003/0009530 A1 | 1/2003 | Philonenko et al. |
| 2003/0028399 A1 | 2/2003 | Davis et al. |
| 2003/0055684 A1 | 3/2003 | Jaskolski et al. |
| 2003/0058838 A1 | 3/2003 | Wengrovitz |
| 2003/0065738 A1 | 4/2003 | Yang |
| 2003/0135565 A1 | 7/2003 | Estrada |
| 2003/0135624 A1 | 7/2003 | McKinnon et al. |
| 2003/0179743 A1 | 9/2003 | Bosik et al. |
| 2003/0191685 A1 | 10/2003 | Reese |
| 2003/0200226 A1 | 10/2003 | Wells et al. |
| 2003/0208543 A1 | 11/2003 | Enete et al. |
| 2004/0057569 A1 | 3/2004 | Busey et al. |
| 2004/0059603 A1 | 3/2004 | Brown, Jr. et al. |
| 2004/0117215 A1 | 6/2004 | Marchosky |
| 2004/0125938 A1 | 7/2004 | Turcan et al. |
| 2004/0153511 A1 | 8/2004 | Maynard et al. |
| 2004/0193449 A1 | 9/2004 | Wildman et al. |
| 2004/0203906 A1 | 10/2004 | Kato et al. |
| 2004/0220830 A1 | 11/2004 | Moreton et al. |
| 2004/0249776 A1 | 12/2004 | Horvitz et al. |
| 2005/0027788 A1 * | 2/2005 | Koopmans et al. ........... 709/200 |
| 2005/0035862 A1 | 2/2005 | Wildman et al. |
| 2005/0065817 A1 | 3/2005 | Mihai et al. |
| 2005/0097176 A1 | 5/2005 | Schatz et al. |
| 2005/0154792 A1 | 7/2005 | Deryugin et al. |
| 2005/0209891 A1 | 9/2005 | Jacobus et al. |
| 2007/0037605 A1 | 2/2007 | Logan |
| 2012/0106728 A1 | 5/2012 | Ghaffari et al. |

* cited by examiner

VIRTUAL PHYSICIAN OFFICE SYSTEMS AND METHODS

CROSS REFERENCE TO RELATED APPLICATIONS

This application is a continuation of U.S. application Ser. No. 11/805,104 filed May 22, 2007 and now issued as U.S. Pat. No. 8,712,031, which is a continuation of U.S. application Ser. No. 10/351,801 filed Jan. 27, 2003 and now issued as U.S. Pat. No. 7,248,688, with both applications incorporated herein by reference in their entireties.

NOTICE OF COPYRIGHT PROTECTION

A portion of the disclosure of this patent document and its figures contain material subject to copyright protection. The copyright owner has no objection to the facsimile reproduction by anyone of the patent document or the patent disclosure, but the copyright owner otherwise reserves all copyrights whatsoever.

BACKGROUND OF THE INVENTION

1. Field of the Invention

This invention generally relates to computer networks and to telephony. More particularly, this invention is directed to methods and systems for more efficient and effective physician practice management of electronic data in a network-based communications system.

2. Description of the Related Art

In *Epidemics*, Hippocrates wrote "[t]he art of medicine has three factors: the disease, the patient and the physician." Were he writing today, the Father of Medicine would also likely include "access to healthcare information" as a fourth factor. Why? Because today's healthcare marketplace is driven by increasing pressure for cost controls, by the increased strength of the consumer voice, by a shift from hospital inpatient care towards primary, ambulatory, and home care, by an emphasis on "case management," by increased competition, and by the focus on quality that is necessary for better patient care. This relentless drive to improve efficiencies and cut costs makes many traditional procedures inefficient. This relentless drive also presents great opportunities for healthcare professionals, organizations, patients, and others to enter into new types of multi-institution partnerships (e.g., strategic alliances between physicians' offices, hospitals, clinics, labs, diagnostic centers, medical record repositories, insurers, patients, pharmaceutical and surgical suppliers, other vendors, etc.) that utilize many different computing systems and other communications technologies to manage and share electronic healthcare information. One of the biggest barriers facing these multi-institution partnerships is creating and maintaining a network-based system that manages efficient, effective, and secure access to standardized or otherwise compatible electronic healthcare information and communications (e.g., able to be presented over a variety of different software and hardware platforms).

Thousands, if not hundreds of thousands or more, of electronic documents, emails, and proprietary information are generated each day and shared among these multi-institution partnerships and non-participants. For example, a physician might order a complex lab test from the local hospital. Instead of waiting for the results to arrive by hand delivery, the physicians' office may get online and request the test results via secure, encrypted email. The hospital's lab staff either manually attaches the lab result to a return email, or, in more advanced systems, the lab system responds automatically to the request and returns the results to a legacy system accessible by the physician. Another example is when a physician needs to admit a patient to the hospital. Instead of having the staff call the admission office and spend upwards of thirty (30) minutes talking and waiting on hold, the office sends the pre-admission information electronically, including patient record information and pre-admission orders to the hospital via an email attachment or directly to the hospital's legacy system. As used herein, the term "legacy system" or "legacy systems" includes data processing, storage, management, and information systems, communications devices, and other network components, such as, for example, databases of electronic patient health history, patient insurance information, demographic information, and physical records. Typically, each legacy system is customized in terms of software, hardware, and network configuration for each participant. Typically, each legacy system includes a network of multiple computer systems (e.g., personal computers, personal digital assistants, and other communications devices); however, the legacy system may also be a stand-alone computer system.

In the above examples, the shared electronic data may be processed in a variety of ways. For example, the hospital may provide information to the physician by transmitting data over a Local Area Network (LAN) connection into a database on a web server. This healthcare information could then be transmitted to a computer system (e.g., personal computer or "PC") of the physician office legacy system over a data connection, such as the Internet, Intranet or Extranet, or over a direct connection, such as dial up access, using push technology that automatically broadcasts the data to the physician's computer system and allows the physician to view the transmitted healthcare data using an appropriate software package, such as a browser, or by using an applet. Thus far, there have not been any network-based systems that facilitate standardized and/or otherwise compatible, secure communications between and among multiple legacy systems and non-legacy systems (e.g., a communications device of a non participant) as well as provide reliable server-based network applications.

In addition to the challenges above, most of the participants and non-participants must also comply with a variety of federal, state, local and other rules that protect the privacy and security of healthcare information associated with a patient. For example, the Health Insurance Portability and Accountability Act (HIPAA), signed into law by President Clinton on Aug. 21, 1996 (Pub. L. 104-191, 110 Stat. 1936), covers health plans, healthcare clearinghouses, and healthcare providers who conduct certain financial and administrative transactions (e.g., electronic billing and funds transfers) electronically. Providers (e.g., physicians, hospitals, etc.) and health plans are required to give patients a clear written explanation of how a covered entity may use and disclose a patient's healthcare information. Further, healthcare providers are required to obtain patient consent before sharing information for treatment, payment, and healthcare operations. In addition, HIPPA also requires that a provider adopt and implement privacy procedures to ensure the privacy and security of the healthcare information.

The above discussion illustrates how the sharing and management of healthcare information (including communications, data, and/or other electronic transmissions) and technology between and among multiple communications devices (of participants and non-participants) is creating a new foundation for a virtual healthcare setting. With this emerging virtual healthcare setting, what are needed are improved network-based healthcare systems and methods that integrate communications infrastructures of each participant to build a secure, integrated, network-based system accessible by participants and non-participants to support different organizational needs and capitalize on emerging trends in the healthcare setting. In addition, the network-based system should provide efficient networked-based healthcare practice management applications that leverage the assets of each legacy system. Accordingly, integrated, network-based healthcare systems and methods are needed that enable sharing, transferring, accessing, and managing standardized or otherwise compatible data and communications with multiple legacy systems. Further, a need exists to improve notification, access, and management of the electronically shared healthcare information and communications without investing millions of dollars in computer equipment, in a networking infrastructure, in maintenance, and in training while also complying with security, authenticity, and/or privacy requirements.

BRIEF SUMMARY OF THE INVENTION

The aforementioned problems and others are reduced by virtual physician office ("VPO") systems and methods that provide more efficient and effective management of electronic healthcare communications (including audio, video, text, and/or digital data) within a network-based communications systems. The VPO leverages the assets of a telecommunications network, a data network, and/or other communications network of a legacy system associated with each participant in a multi-institutional partnership to facilitate improved access, sharing, notification, security, and/or management of electronic healthcare communications. Some advantages of VPO include increased ability to flexibly manage, bill, and track physician services, faster access to electronic healthcare communications and/or data shared among or between multiple legacy systems, and increased ability to share electronic healthcare data among or between different networks of communications devices. In addition, the VPO utilizes proprietary network-based systems (depending on how a physicians' office and/or a physician's home accesses the VPO) to reduce or prevent electronic healthcare data and/or communications from entering traffic in a public data network, such as the Internet. If electronic healthcare data and/or communications are routed over a public data network, then the VPO may utilize encryption and/or other secure technologies to protect and keep private the contents of the data and/or communication.

An embodiment of this invention describes a method that includes receiving an electronic healthcare communication associated with a physician office legacy system to a network-based communications system, categorizing the electronic healthcare communication, and using a physician practice management application to process the electronic healthcare communication. The network-based communications system enables an exchange of the electronic healthcare communication between the physician office legacy system and one or more networks of communications devices associated with a telecommunications service provider. Typically, the physician practice management application runs on a server associated with the network-based communications system, such as a central office ("CO") of a public switched telecommunications network ("PSTN") and/or of a mobile switching center of a mobile switching telecommunications office ("MSTO").

Other embodiments describe methods that include establishing a first data connection between a communications device of a physician office legacy system and a network-based communications system, receiving an electronic healthcare communication from the communications device over the data connection, accessing a physician practice management application, using the physician practice management application to manage the electronic healthcare communication, establishing a second data connection, and communicating the electronic healthcare data via the first data connection and the second data connection. According to an embodiment, the second data connection is established between the network-based communications system and a second legacy system. According to another embodiment, the second data connection is established between the network-based communications system and a non-affiliated (e.g., non-participant of the multi-institutional partnership) communications device. In both embodiments, the second data connection uses a rule-based application dataserver to categorize the electronic healthcare into one or more of the following categories: (1) data associated with an access agent, (2) data associated with a security agent, (3) data associated a messaging/communications agent, (4) data associated with a transactional agent, (5) data associated with a troubleshooting agent, and (6) data associated with an application agent.

Still further, this invention describes a system that includes a network of legacy systems, a physician practice management application for managing electronic healthcare communications associated with at least one of (i) a calendar and schedule, (ii) patient information, (iii) charges and fees, (iv) receipts, (v) laboratory testing, (vi) prescriptions, (vii) reports, (viii) office facilities and maintenance, (ix) compliance and inspections, (x) patient triage and medical protocols, (xi) on-call services, (xii) insurance billing and appeals, (xiii) patient billing, and (xiv) back-up storage settings, and a rule-based application dataserver for managing the exchange of electronic healthcare data with the legacy system, the rule-based application dataserver provided by the telecommunications service provider.

BRIEF DESCRIPTION OF THE SEVERAL VIEWS OF THE DRAWINGS

The above and other embodiments, objects, uses, advantages, and novel features of this invention are more clearly understood by reference to the following description taken in connection with the accompanying figures, wherein.

DETAILED DESCRIPTION OF THE INVENTION

This invention now will be described more fully hereinafter with reference to the accompanying drawings, in which exemplary embodiments are shown. This invention may, however, be embodied in many different forms and should not be construed as limited to the embodiments set forth herein; rather, these embodiments are provided so that this disclosure will be thorough and complete, and will fully convey the scope of the invention to those of ordinary skill in the art. Moreover, all statements herein reciting embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure).

Thus, for example, it will be appreciated by those of ordinary skill in the art that the diagrams, schematics, flowcharts, and the like represent conceptual views or processes illustrating systems and methods embodying this invention. The functions of the various elements shown in the figures may be provided through the use of dedicated hardware as well as hardware capable of executing associated software. Similarly, any switches shown in the figures are conceptual only. Their function may be carried out through the operation of program logic, through dedicated logic, through the interaction of program control and dedicated logic, or even manually, the particular technique being selectable by the entity implementing this invention. Those of ordinary skill in the art further understand that the exemplary hardware, software, processes, methods, and/or operating systems described herein are for illustrative purposes and, thus, are not intended to be limited to any particular named manufacturer.

Figure 1:
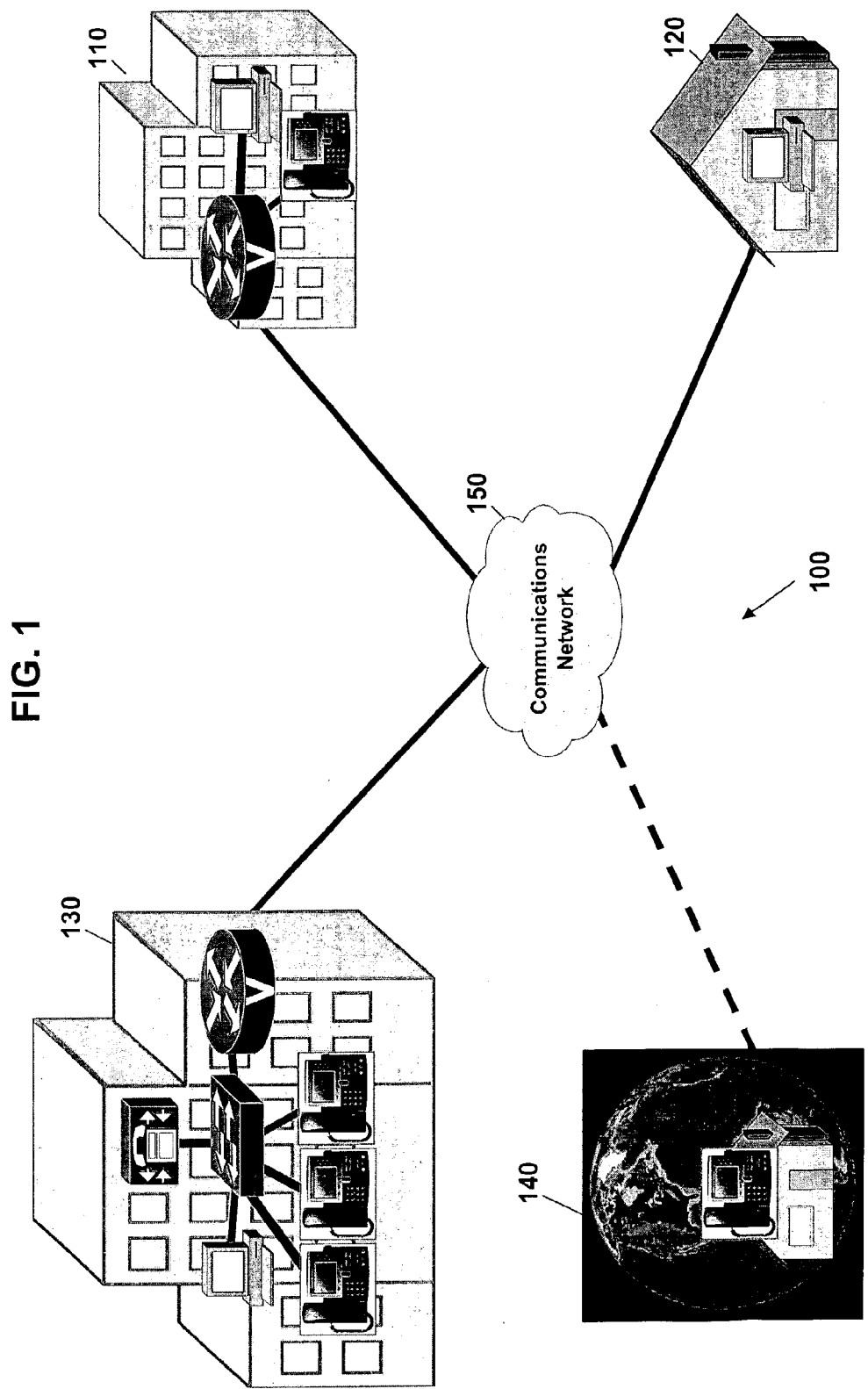
FIG. 1 is a schematic illustrating an overview of an exemplary operating environment of a virtual physician office (VPO) according to an embodiment of this invention.

Referring now to FIG. 1, a virtual physician office (VPO) 100 typically includes a physician's or physicians' office 110, a home office of a physician 120, other related client, vendor, and service-oriented participants 130 of a multi-institutional partnership (including the physicians' office) and of non-participants 140 that leverage the assets of a network-based communications network. The purpose of the VPO 100 is to efficiently share information over a variety of communications devices, automate business and transactional processes, and enhance market position. In the case of a VPO, participants 110, 120, 130 and non-participants 140 may include local hospitals, insurance companies, HMOs, affiliated hospitals, clinics, affiliated physicians' offices, medical schools, universities, and strategic partners. Patients, as well as vendors, could also be included, as could service providers, such as clinical laboratories, pharmacy services, temporary agencies, private ambulance services, and subspecialty services. After all, rapid communication and exchange of information between these entities (e.g., participants including the doctor's office and including non-participants) can make a critical difference in the quality of patient care. In most cases, each participant usually has its own legacy system, including software, hardware, equipment, networks, and/or other information technology assets. For example, a large physicians' office commonly has a local and/or a wide area network that utilizes Ethernet, dedicated private lines, Frame Relay, ISDN, ATM, ADSL, and the like. Further, these legacy systems provide an interface to the communications network 150, such as, for example, a data network, such as the Internet, Intranet, and/or Extranet, that may be locally or remotely accessed by a participant's user (e.g., an employee using a computer system within the physician office legacy system).

This invention provides an efficient networked-based physician practice management application that leverages the assets of each legacy system. The VPO 100 provides improved access, sharing, notification, routing, security, and/or management of electronic healthcare communications and/or data associated with the physician practice management application. Typically, the electronic healthcare communication and/or data contains fields, files, or other electronic indexing that cross-references multiple agents (e.g., Access Agent, Security Agent, Messaging Agent, Transaction Agent, Troubleshooting Agent, and Application Agent) of a rule-based application dataserver. This indexing as well as other information that may be gathered from the incoming communication signal (e.g., ICLID) and/or interactive information input by the sender of the communication are used to associate the communications and/or data. As discussed in more detail below, the communications network 150 uses a rule-based application dataserver preferably provided by a telecommunications service provider, and also uses an integrated delivery system (IDS) to process exchanged healthcare information into a selected legacy system and/or to present the electronic healthcare communication (including associated data) to a communications device. As used herein, the term "electronic healthcare communication" includes audio, video, text, and/or digital communications including electronic healthcare communications such as email, attached files (e.g., an attached file to the email), and compatible data formats (e.g., a file that has been processed by the rule-based application dataserver and the IDS to format and/or standardize electronic information shared between legacy systems and/or between the network-based communications system and a communications device). The term "electronic healthcare communication" also includes transaction notifications and/or transaction replies generated by the rule-based application dataserver and/or the IDS, and/or other means of communicating electronic information between or among participants and non-participants. Also, as used herein, the term "communications device" includes electronic devices that may be used to communicate audio, video, text, and/or digital communications, such as a personal (PC) computer system, plain old telephone (POTS) phone, a wireless communications device, a mobile phone, a cellular phone, a wide area protocol (WAP) phone, a satellite phone, a modem, a pager, a digital music device, a digital recording device, a personal digital assistant (PDA), an interactive television, a digital signal processor (DSP), a Global Positioning System (GPS) device, and combinations thereof. Typically, a telecommunications service provider (e.g., local service provider, long distance service provider, wireless service provider) provides telecommunications service to the communications device and, thus, is associated with the communications device.

Figure 2:
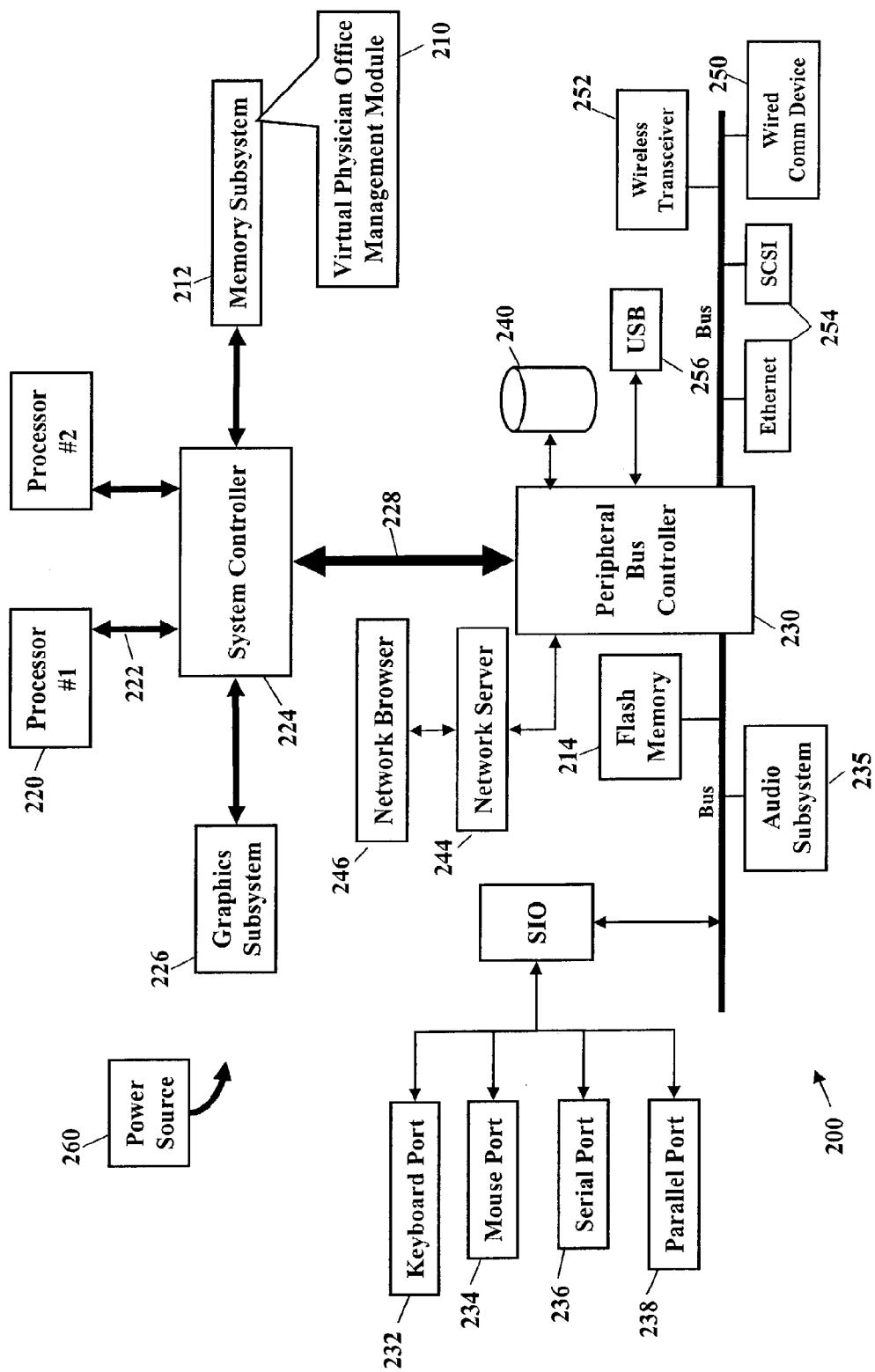
FIG. 2 is a block diagram showing of a VPO Management Module that resides in a computer system according to an embodiment of this invention.

FIG. 2 is a block diagram showing a VPO Management Module 210 residing in a computer system 200. The VPO Management Module 210 operates within a system memory device. The VPO Management Module 210, for example, is shown residing in a memory subsystem 212. The VPO Management Module 210, however, could also reside in flash memory 214 and/or in a peripheral storage device, such as storage device 240. The computer system 200 also has one or more central processors 220 executing an operating system.

The operating system, as is well known, has a set of instructions that control the internal functions of the computer system 200. A system bus 222 communicates signals, such as data signals, control signals, and address signals, between the central processors 220 and a system controller 224 (typically called a "Northbridge"). The system controller 224 provides a bridging function between the one or more central processors 220, a graphics subsystem 226, the memory subsystem 212, and a PCI (Peripheral Controller Interface) bus 228. The PCI bus 228 is controlled by a Peripheral Bus Controller 230. The Peripheral Bus Controller 230 (typically called a "Southbridge") is an integrated circuit that serves as an input/output hub for various peripheral ports. These peripheral ports could include, for example, a keyboard port 232, a mouse port 234, a serial port 236 and/or a parallel port 238. Additionally, these peripheral ports would allow the computer system 200 to communicate with a variety of communications devices through ports (such as a SCSI port and/or an Ethernet port, shown as reference numeral 254), a Wireless Transceiver port 252 (using the IEEE Wireless standard 802.11, Infrared, the Industrial and Scientific band of the electromagnetic spectrum, or any other portion of that same spectrum), and a Wired Comm Device Port 250 (such as modem V90+ and compact flash slots). The Peripheral Bus Controller 230 could also include an audio subsystem 235. Additionally, the computer system 200 may interface with a network server 244 operating with a network browser 246. The network server 244 and the network browser 246 may be stand alone or integrated components. Still further, the computer system 200 may include a power source 260, such as a rechargeable battery to provide power and allow the computer system 200 to be portable. The power source 260 may additionally or alternatively include an alternating current (AC) power source or power converter.

The processor 220 is typically a microprocessor. Advanced Micro Devices, Inc., for example, manufactures a full line of microprocessors, such as the ATHLON™ (ATHLON™ is a trademark of Advanced Micro Devices, Inc., One AMD Place, P.O. Box 3453, Sunnyvale, Calif. 94088-3453, 408.732.2400, 800.538.8450, www.amd.com). Sun Microsystems also designs and manufactures microprocessors (Sun Microsystems, Inc., 901 San Antonio Road, Palo Alto Calif. 94303, www.sun.com). The Intel Corporation manufactures microprocessors (Intel Corporation, 2200 Mission College Blvd., Santa Clara, Calif. 95052-8119, 408.765.8080, www.intel.com). Other manufacturers also offer microprocessors. Such other manufacturers include Motorola, Inc. (1303 East Algonquin Road, P.O. Box A3309 Schaumburg, Ill. 60196, www.Motorola.com), International Business Machines Corp. (New Orchard Road, Armonk, N.Y. 10504, (914) 499-1900, www.ibm.com), and Transmeta Corp. (3940 Freedom Circle, Santa Clara, Calif. 95054, www.transmeta.com).

The preferred operating system is the UNIX® operating system (UNIX® is a registered trademark of the Open Source Group, www.opensource.org). Other UNIX-based operating systems, however, are also suitable, such as LINUX® or a RED HAT® LINUX-based system (LINUX® is a registered trademark of Linus Torvalds, and RED HAT® is a registered trademark of Red Hat, Inc., Research Triangle Park, N.C., 1-888-733-4281, www.redhat.com). Other operating systems, however, are also suitable. Such other operating systems would include a WINDOWS-based operating system (WINDOWS® is a registered trademark of Microsoft Corporation, One Microsoft Way, Redmond Wash. 98052-6399, 425.882.8080, www.Microsoft.com). and Mac® OS (Mac® is a registered trademark of Apple Computer, Inc., 1 Infinite Loop, Cupertino, Calif. 95014, 408.996.1010, www.apple.com).

The system memory device (shown as memory subsystem 212, flash memory 214, or peripheral storage device 240) may also contain one or more application programs. For example, an application program may cooperate with the operating system and with a video display unit (via the serial port 236 and/or the parallel port 238) to provide a Graphical User Interface (GUI) display for the VPO Management Module 210. The GUT typically includes a combination of signals communicated along the keyboard port 232 and the mouse port 234. The GUI provides a convenient visual and/or audible interface with the user of the computer system 200. As is apparent to those of ordinary skill in the art, the selection and arrangement of the VPO Management Module 210 may be programmed over a variety of alternate mediums, such as, for example, a voice-activated menu prompt.

The VPO Management Module 210 allows the physicians' office 110 (and/or physician home 120) to manage VPO services, such as: (1) allowing a user (e.g., an authorized staff member associated with the physician office legacy system) to customize rules and user groups associated with each practice management application including the physician practice management application; (2) allowing the user to customize rules and user groups associated with a rule-based engine of the rule-based dataserver; (3) allowing the user to customize presentation, features, and/or management of an incoming electronic healthcare communication (e.g., an email, an attached file, a compatible second data format, a transaction reply, a transaction notification, and/or other electronic communications); and (4) allowing the user to control routing and integration of the electronic healthcare communication within and between the physician office legacy system, other legacy systems, and non-participant communications device. For example, the user may select an Access Agent having a user group list to add, delete, or modify physician office staff information, such as, associated service node addresses, IP addresses, email addresses, and/or other electronic address information of communications devices associated with the physicians' office legacy system (e.g., the phone number of the communications device, such as a doctor's cell phone number, is input into a communications profile to identify the communications device with the physicians' office legacy system). For example, an address of the user group list may be associated with the electronic healthcare communication and act as a trigger (similar to decoding an ICLID signal for telecommunication special service features offered by telecommunication service providers) to automatically send the electronic healthcare communication to the VPO rule-based application dataserver and to automatically open one or more of the network-based practice management applications with the communication. The VPO Management Module 210 also allows the user to customize features, such as electronic healthcare communication handling options. For example, the VPO Management Module 210 may split a user's screen into two viewing areas and present the incoming electronic healthcare communication in one portion and present the physician practice management application in the second portion. Further, the VPO Management Module 210 may allow the user to control whether to accept, decline, or postpone integration of a compatible data format into the physician office legacy system (or a legacy system of another participant or a communications device of a non-participant) or might be set to automatically accept, decline, or postpone integration depending on a participant's address or on an address of the non-participant's communications device. Still further, the VPO Management Module 210 of the computer system 200 may provide the IP address or the like so that the communications network 150 can communicate the electronic healthcare communication, and, thus integrate telephony events and data network events with the legacy system and/or the non-participant's communications device. Further, the VPO Management Module 210 may interact and/or otherwise interface with a telecommunications network-based information systems (NBIS) management module that controls access, sharing, notification, security, and/or management of electronic healthcare data exchanged between or among different legacy systems of participants. The NBIS Management Module and related methods and systems are disclosed in applicants' co-pending U.S. patent application Ser. No. 10/253,500 entitled "Network-Based Healthcare Information Systems," filed Sep. 24, 2002, and of which the "Brief Summary of the Invention" and "Detailed Description of the Invention" sections are incorporated herein by this reference. Still further, the VPO Management Module 210 may interact and/or otherwise interface with a healthcare Virtual Private Network (VPN) Management Module that controls access, sharing, notification, security, and/or management of electronic healthcare data exchanged between or among different legacy systems and communications devices of non-participants. The VPN Management Module and related methods and systems are disclosed in applicants' co-pending U.S. patent application Ser. No. 10/353,126 entitled "Healthcare Virtual Private Network Methods and Systems," filed simultaneously herewith, and of which the "Brief Summary of the Invention" and "Detailed Description of the Invention" sections are incorporated herein by this reference.

Figure 3:
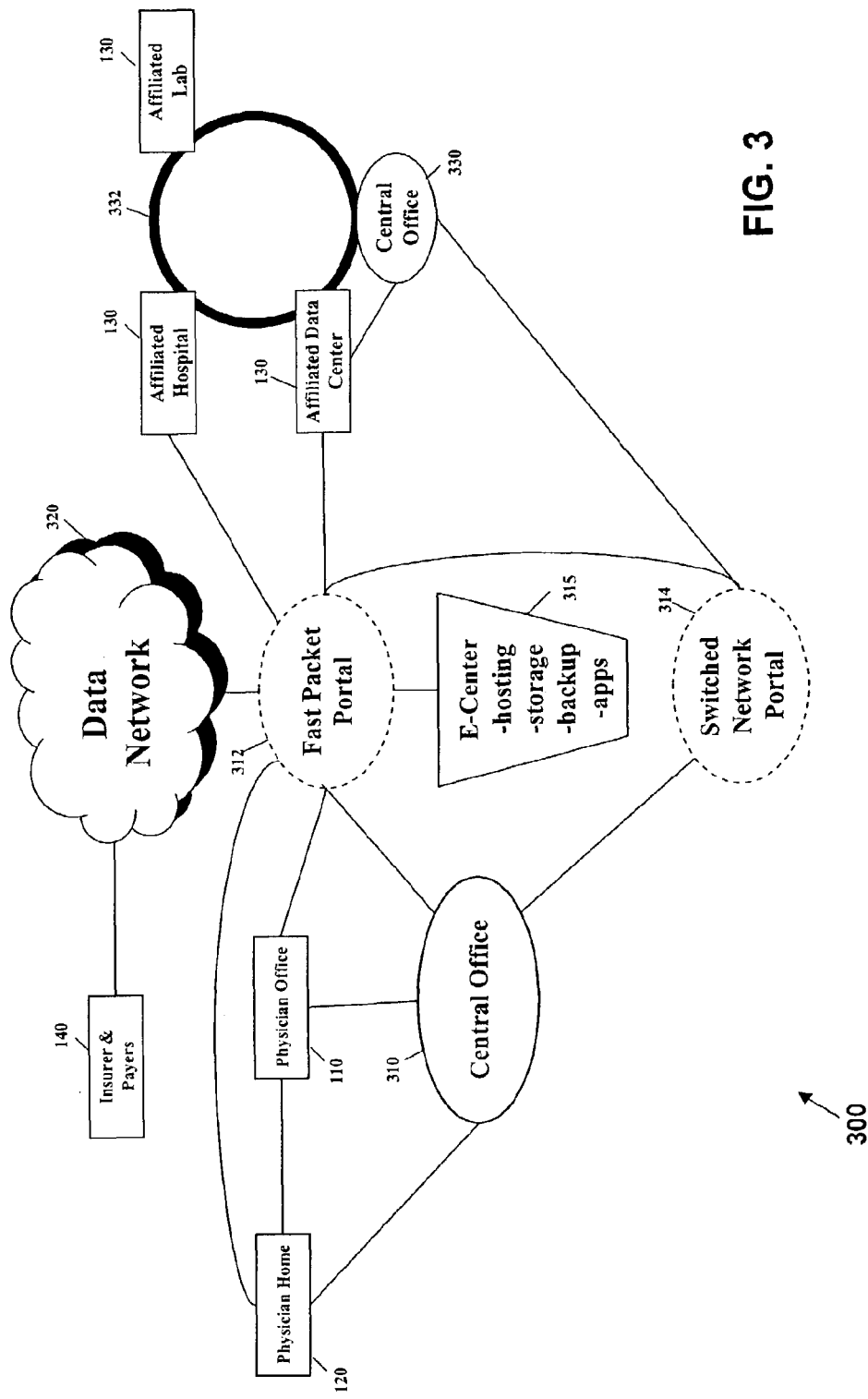
FIG. 3 is a schematic showing a detailed schematic of an operating environment for a VPO system according to an embodiment of this invention.
Figure 4:
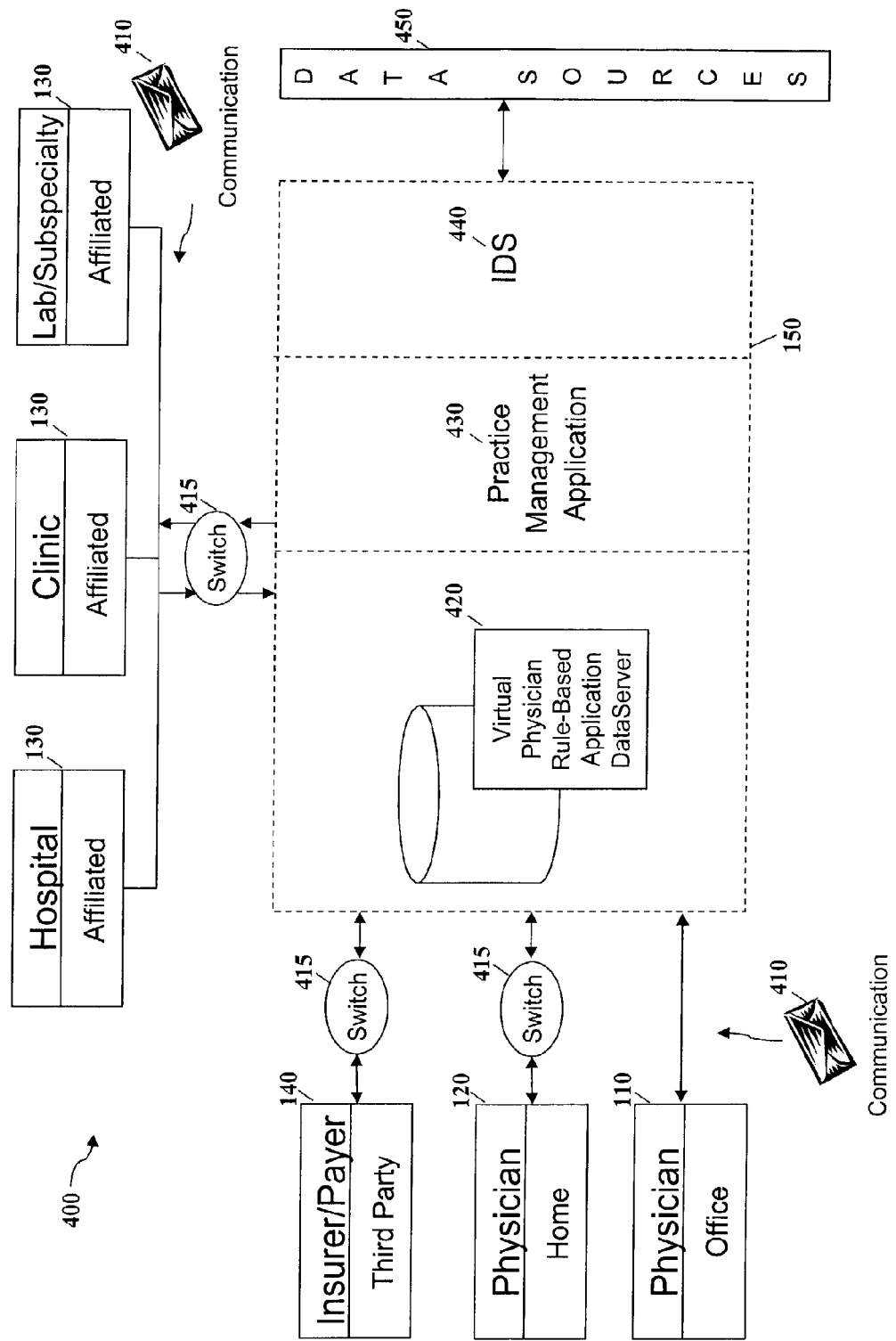
FIG. 4 is a schematic showing a detailed schematic of another operative environment for a VPO system according to an embodiment of this invention.

The VPO Management Module 210 further allows the physicians' office 110 to control access, sharing, notification, routing, security, management, and/or additional processing of electronic healthcare communications within an application (such as practice management application 430 of FIG. 4). Typically, the application is hosted by the communications network 150 via e-center 315. Thus, the VPO 100 allows the application to be customized to share electronic healthcare communications with a variety of communications devices of the physicians' office legacy system, other legacy systems, and non-participants. In addition, the VPO Management Module 210 may allow the physicians' office (via an authorized user/staff member) 110 to control how the data (i.e., the electronic healthcare communication and/or associated data) is further processed by the application including (1) sending the data to a local storage device (such as database 240 of FIG. 2), or alternatively, to a remote storage device (such as affiliated data center 130 or e-center 315 of FIG. 3), (2) instructions for archiving the data (e.g., data compression, duration of storage, etc.), (3) encrypting the data, (4) copying the data, and (5) associating the data with a VPO rule-based profile (such as VPO rule-based profile 500 of FIG. 5). The VPO Management Module 210 may be downloaded from a telecommunications network, a data network, or provided on a storage media (e.g., diskette, CD-ROM, or installed by the computer system manufacturer) to install on the computer system 200 to enable, disable, and further control a variety of VPO services.

Figure 5:
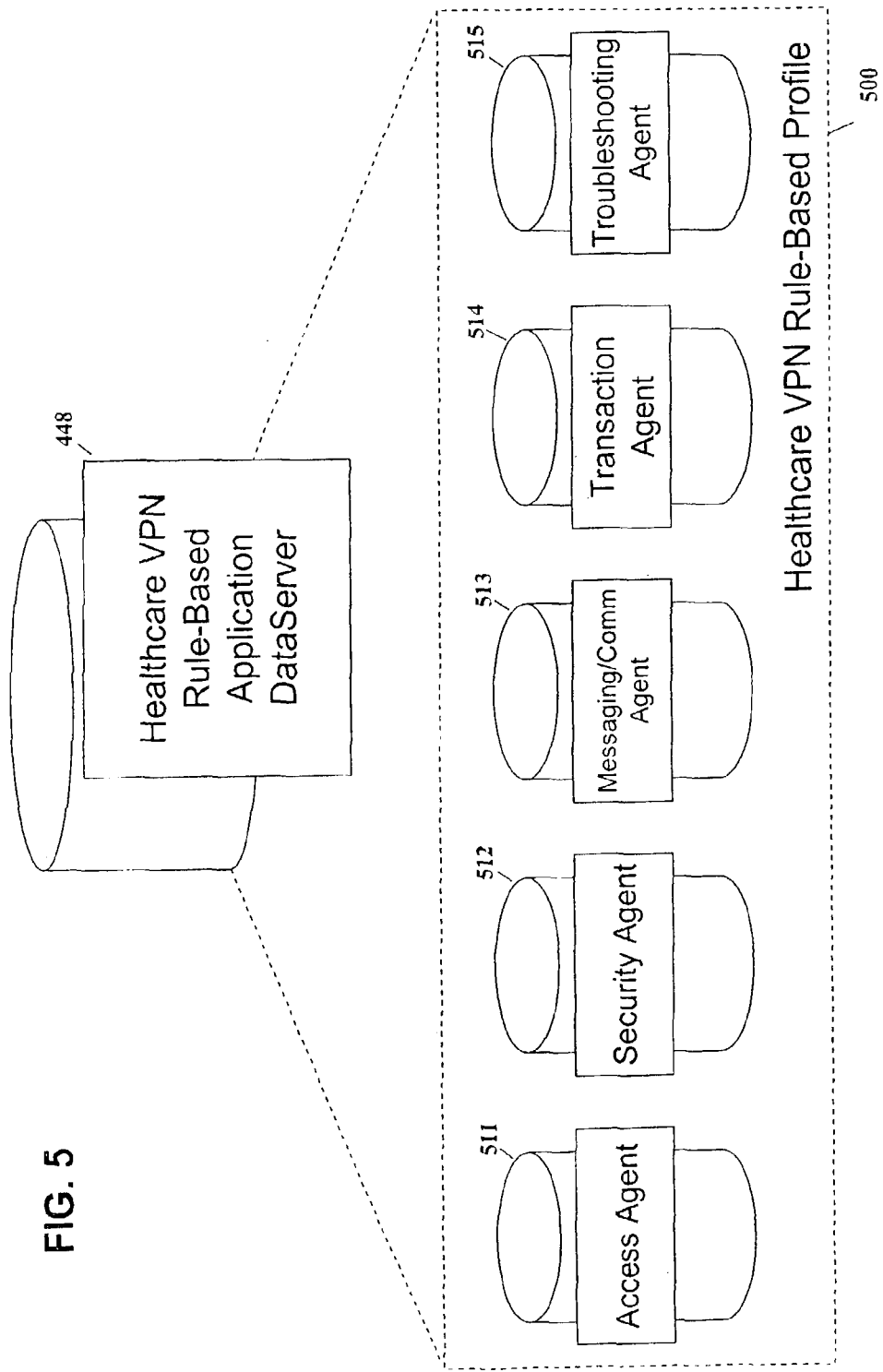
FIG. 5 is a detailed schematic of the VPO vile-based application dataserver residing in the network-based communications system shown in FIG. 1.
Figure 6:
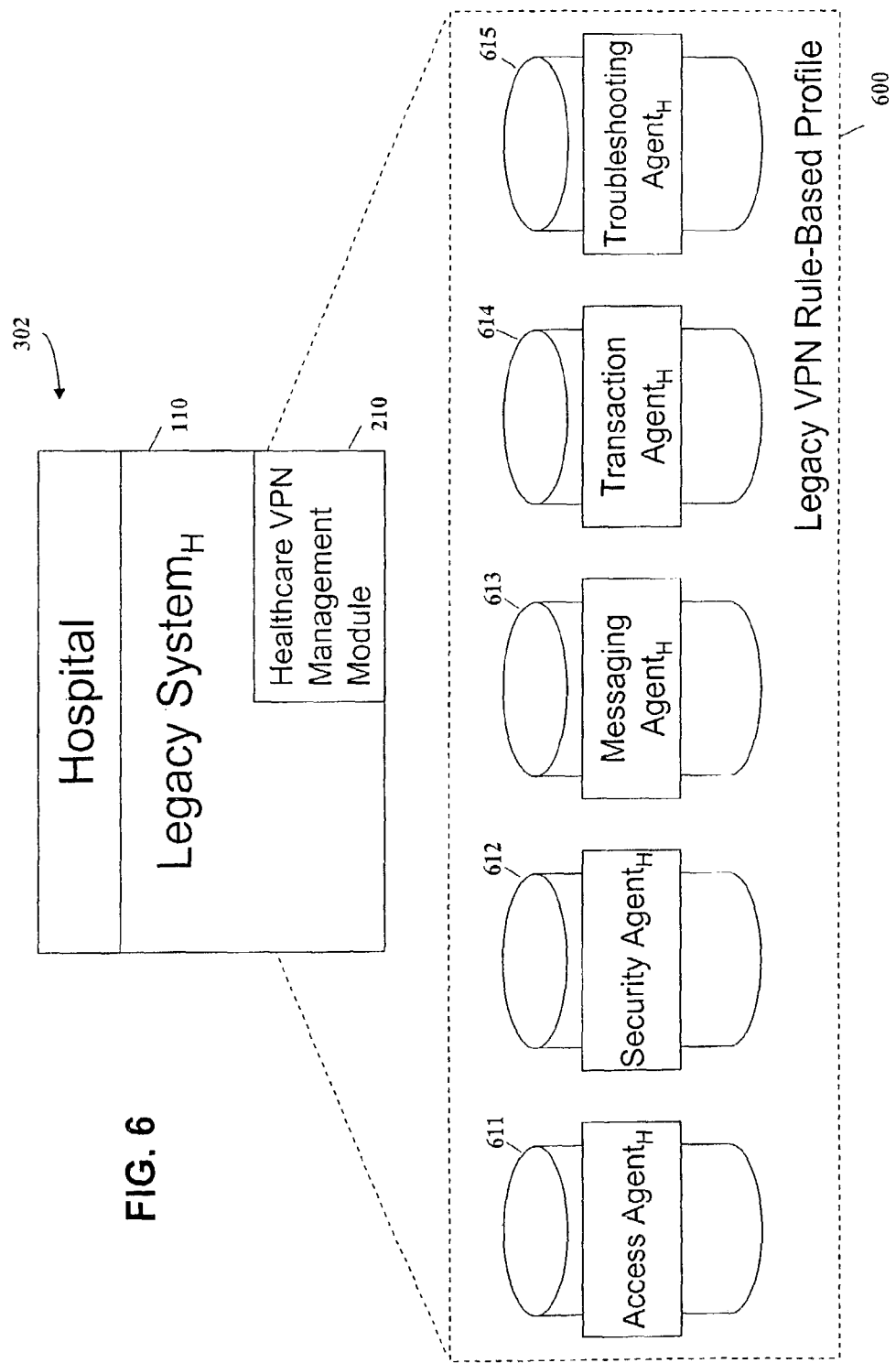
FIG. 6 is a detailed schematic of a VPO rule-based profile residing in the physician office legacy system shown in FIG. 1.
Figure 7:
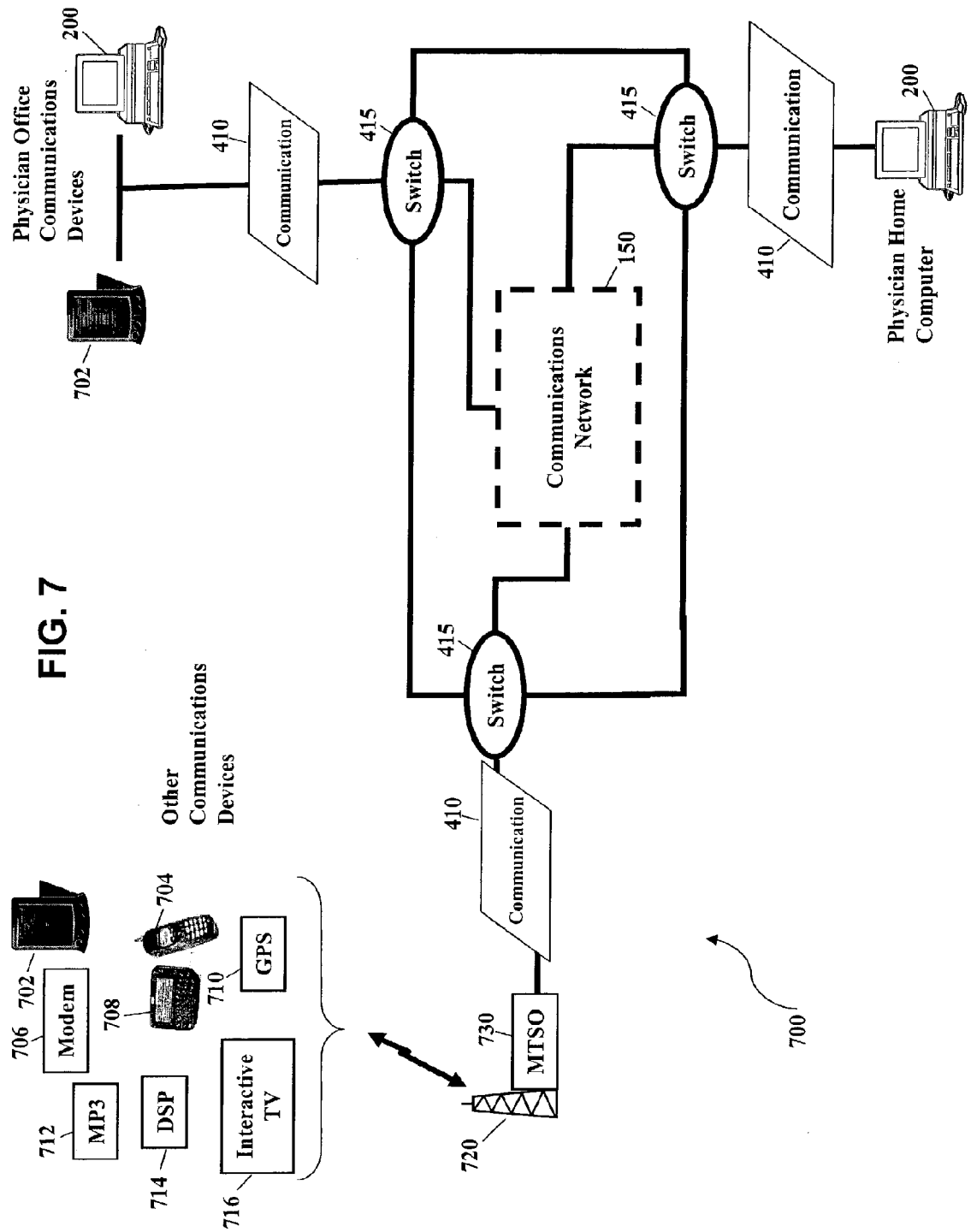
FIG. 7 is a schematic showing an exemplary embodiment of communicating an electronic healthcare communication using wired and wireless communications devices associated with the VPO according to an embodiment of this invention.
Figure 8:
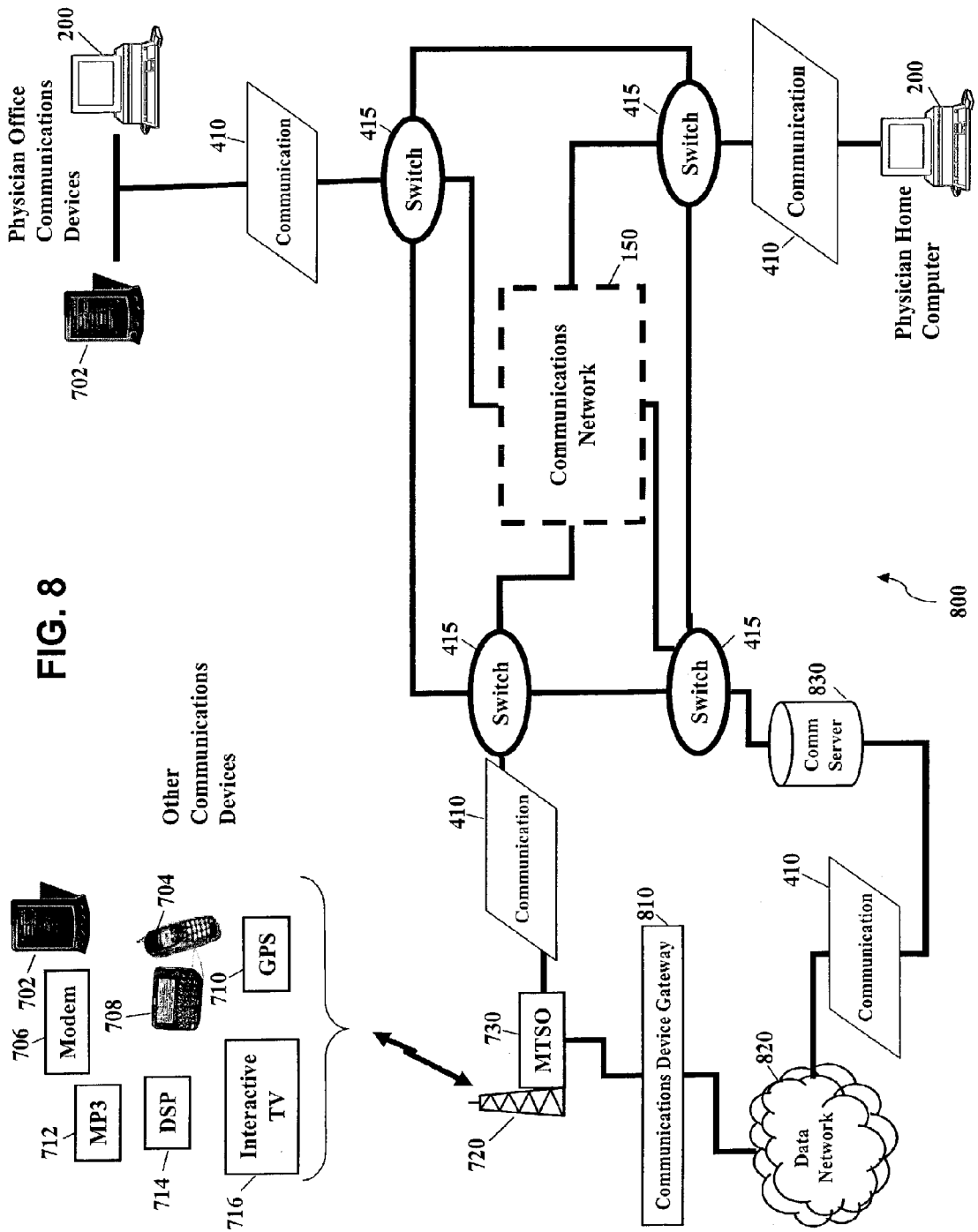
FIG. 8 is a schematic showing another exemplary embodiment of communicating an electronic healthcare communication using wired and wireless communications devices associated with the VPO according to an embodiment of this invention.

Referring to FIGS. 3-8, the VPO 300 includes a legacy system associated with the physicians' office 110 and/or physicians' home 120, at least one legacy system of other participants (e.g., affiliated hospital, affiliated lab, and/or affiliated data center) 130, at least one communications device (and/or information system) of a non-participant (e.g., insurer and/or payer) 140, a first central office 310 connected with the physicians' office 110 and/or home 120, fast packet portal 312, switched packet portal 314, an electronic center ("e-center) 315, a data network 320, and a second central office 330 connected with other participants 130. Communications devices of the legacy systems (e.g., legacy systems of participants 110, 120, 130) and of the non-participants are not shown in FIG. 3; however, specific exemplary communications devices are shown in FIGS. 7-8 and include computer 200, personal digital assistant (PDA) 702, wireless phone 704, modem 706, interactive pager 708, global positioning system (GPS) 710, MP3 712, digital signal processor 714, and interactive television 716. Each physicians' office legacy system typically includes at least one computer system 200 and may have the VPO Management Module 210 (including the IP address or other communications address associated with the physicians' office connection to a telecommunications network, data network connection, and/or communications network) residing within the computer system 200. Turning now to FIG. 4, the first central office 310 connected with the physicians' office legacy system and the second central office 330 of the other participants may include a service switching point (SSP) (not shown), a service control point (SCP) (not shown), an Intranet (not shown), and a VPO Rule-Based Application Dataserver 420. Switch 415 allows the connected physicians' office legacy system 110, home 120, other participants' legacy systems 130, and communications devices of non-participants to communicate electronic healthcare communications 410 via the communications network 150. Similarly, each switch 415 allows a connected communications device to communicate electronic healthcare communications 410 via the communications network facility 150. In a preferred embodiment, the communications network facility is a telecommunications network facility. The telecommunications network facility may include the central office (CO) (310, 330 of FIG. 3) a mobile telephone switching office (MTSO) (not shown), and/or a combination CO/MTSO. Further, the communications network facility 150 may use any means of coupling switches 415 to the facility 440, but the coupling means is preferably high-capacity, high-bandwidth optical transport services, Gigabit Ethernet services, and/or the like for digital electronic healthcare communications, such as fast packet portal 312. Other coupling means includes switch network portal 314 typically used for voice and data transmissions. As those of ordinary skill in the art of communications understand, the telecommunications network facility could also link switches 415 of the legacy system (or the communications device of the non-participant) via other appropriate means, such as, for example a Synchronous Optical Network (SONET) structure with redundant, multiple rings. In addition, the telecommunications network facility, legacy systems, communications network, and communications devices may be connected by similar slower lines, such as copper conductors, digital subscriber lines, and the like.

Typically, a user (e.g., staff member of physicians' office) uses computer system 200 to gain access to the communications network 150. For example, if the user wishes to use one or more of the applications 430 and/or send, receive, or access voice, video, and/or data (e.g., read and respond to e-mail, order test results, view video-clips including static images, listen to recorded information, engage in an interactive-diagnosis session, etc.), then the computer system 200 connects with the communications network 150 via switch 415. Alternatively, the computer system 200 may have a dedicated line and directly connect with the communications network. Communications signals associated with the electronic healthcare communication 410 arrive at the communications network 150 and are associated (either by input from the user or by the dataserver) with the physicians' office legacy system 110. The VPO 400 may include wired, optical, and/or wireless elements and may further include private network elements, such as private branch exchanges (PBXs), and/or other elements (not shown). The communications network 150 includes Advanced Intelligent Network (AIN) componentry controlling many features of the network. The communications network 150 and/or switches 415 could also include a packet-based "soft switch" that uses software control to provide voice, video, and/or data services by dynamically changing its connection data rates and protocols types. If the communications network 150 or switches 415 should include a softswitch, the AIN componentry is replaced by an application server that interfaces with the softswitch via a packet protocol, such as Session Initiation Protocol (SIP). The signaling between the computer system 200, the legacy systems 110, 120, 130, the communications device of non-participants 140, the switches 415, the communications network 150 including AIN componentry, data network 320, central offices 310, 320 and the e-center 315, however, are well understood in by those of ordinary skill the art and will not be further described. Further, those of ordinary skill in the art will be able to apply the principles of this invention to their own information and computing systems including their network configurations which may differ substantially from the system shown in the figures.

The VPO Rule-Based Application DataServer 420 allows the physicians' office to activate, de-activate, administer, and/or otherwise manage e-center 315 services including data storage and backup, network-based applications 430, integrated delivery systems 440, and hosting services. In an embodiment, the VPO Rule-Based Application DataServer 420 has the ability to communicate with various networks, including internal and external telecommunications and/or data networks using appropriate protocols, such as standard transmission control protocol and Internet protocol (TCP/IP). The VPO Management Module 210 may be downloaded from an internet service provider (e.g., America On Line (AOL)), the VPO Rule-Based Application DataServer 420, the central offices 310 and 330, and the data network 320. The VPO Management Module may also be provided on a storage media (e.g., diskette, CD-ROM, and/or DVD) or installed by the computer system manufacturer. However the VPO Management Module 210 is obtained, the VPO Management Module 210 is delivered to the physicians' office 110 and installed on the computer system 200 to enable, disable, and further control a variety of the VPO Management Services. Additionally, the non-participant 140 is typically provided an applet and/or a web browser interface for communicating the electronic healthcare communication over the VPO. The applet and/or web-browser operates over the non-participant's communication device to allow the non-participant to control a limited set of commands for VPO Management Services including verification and authentication requirements.

As illustrated by FIG. 4, the flow of the electronic healthcare communication 410 may involve the physicians' office 110 using computer system 200 to create the electronic healthcare communication 410 with or without an attached file and/or associated data. The physicians' office 110 may create the electronic healthcare communication 410 using a variety of software applications including electronic messaging, word processing, and others (e.g., MICROSOFT OUTLOOK® and MICROSOFT WORD®, both registered trademarks of Microsoft Corporation, One Microsoft Way, Redmond Wash. 98052-6399, 425.882.8080, www.Microsoft.com). In an embodiment, the electronic healthcare communication 410 is created by connecting to and accessing the communications network 150 and using the network-based practice management software application 430 (typically provided by a participant application service provider (ASP)). In a preferred embodiment, the network-based application 430 is a physician practice management application providing management of at least one of the following for the physicians' office: (1) a calendar and schedule of physicians and staff including work schedules, appointments, meetings, facilities used for appointments and meetings, and other related information, (2) patient information including medical records and releases, contact information, insurer information, and scheduled appointments, (3) charges and fees for billing insurers and other payers (e.g., patient, employer, guardian, etc.), (4) receipts for services provided by the physician office and products purchased by the physician office, (5) laboratory testing including laboratory contact information, work schedule, requirements for lab specimens, fees and charges, and other information, (6) prescriptions including a drug information, pharmacy contact information, new research for drugs on the market and drugs not yet on the market, and other related information, (7) reports, (8) office facilities and maintenance including facility administration such as loans for equipment, rental information, cleaning services, and other information, (9) compliance and inspections for federal, state, and local regulations governing the physician practice, (10) patient triage and medical protocols, (11) on-call services including schedules of physicians and staff responsible for handling call, contact numbers, and contact information for hospitals that will admit patients (including hospitalists to admit the patient, if necessary), (12) insurance appeals for processing insurance claims that are returned, (13) billing and financial management services including patient billing, payroll, building rent, equipment rental, and other accounting, and (14) back-up storage settings for redundant storage of the information in items (1)-(13). A stand alone, exemplary physician practice management application that provides a portion of some of these management features is HEALTHBILLRX offered by HealthCentrics, One Northside 75, Suite 120, Atlanta, Ga. 30318, 404.609.5070, www.healthcentrics.com). The electronic healthcare communication 410 may be created using an applet, a web browser, and/or the VPO Management Module 210 residing on computer system 200 to interact and input information (including the electronic healthcare communication and/or related data) with the application 430. Further, the application 430 may include and/or interface with the IDS 440. After the electronic healthcare communication is received by the communications network 150, the VPO Rule-Based DataServer 420 determines whether external data sources (e.g., affiliated data center 130, a database of affiliated hospital 130, etc.) need to be queried for related electronic healthcare data or for retrieving a file that is linked rather than attached to the electronic healthcare communication 410, and, if so, retrieves the related data. Next, the communications network 150 interprets the electronic healthcare communication 410 including any attached files, related healthcare data, and/or the linked files using network elements including the VPO Rule-Based Application DataServer 420. Thereafter, the VPO Rule-Based Application DataServer 420 routes the electronic healthcare communication (e.g., the attached file, related healthcare data, and/or the linked object) 410 to the IDS 440 so that the electronic healthcare communication 410 may be interpreted for compatible exchange with a participant's legacy system 110, 120, 130 and/or a communications device of a non-participant 140. The IDS 440 may be a stand alone system (not shown in the figures), the IDS 440 may be integrated into the communications network 150 (as shown in FIG. 4), the IDS 440 may be integrated with one of the participant's legacy systems (not shown in the figures) that is accessed by the communications network 150 or data network 320, or the IDS 440 may be a combination of these systems (not shown). No matter how the IDS 440 is deployed, the electronic healthcare communication 410 and/or data is received, processed so that the electronic healthcare communication 410 and/or data are compatible for the receiving legacy system 110, 120, 130 and/or communications device of the non-participant, and associated with a transaction reply (e.g., a communication to the communications device of a party receiving the electronic healthcare communication 410 including information about the attached file or the compatible data format) or with a transaction notification (e.g., a communication to the communications device of a sending party (e.g., party originating, creating, forwarding, or otherwise sending the communication) about the electronic healthcare communication 410 including information about the attached file or the compatible data format). Thereafter, the transaction reply and/or the transaction notification are routed through the communications network 150 and forwarded to the receiving legacy system or to the non-participant's communications device (not shown). The VPO Management Module 210 (or, alternatively, the practice management application 430 via an interface with the VPO Management Module 210) presents the electronic healthcare communication 410 so that the receiving physicians' office 110 of the computer system 200 has immediate access, notification, and management of the electronic healthcare communication 410 including the compatible data format and updated data in a receiving legacy system 110, 120, 130 and/or communications device of a non-participant 140.

Referring now to FIG. 5, the physicians' office 110 interacts with the VPO Management Module 210 to access and login to the VPO Rule-Based Application DataServer 420 and to establish a VPO Rule-Based Profile 500. The VPO Rule-Based Application DataServer 420 stores one or more VPO Rule-Based Profiles 500 that include data and applications associated with an Access Agent 511, a Security Agent 512, a Messaging/Communications Agent 513, a Transaction Agent 514, a Troubleshooting Agent 515, and an Application Agent 516. For example, the Access Agent 511, Security Agent 512, Messaging/Communications Agent 313, Transaction Agent 514, Troubleshooting Agent 515, and Application Agent 516 may contain a variety of fields and/or files associated with at least one of the following: login information associated with a user (including participants 110, 120, 130, non-participants 130, and/or authorized users), password of the user, telephone number or Service Node of the user (this may include a plurality of addresses that are associated with a Service Node or other switch, such as, for example, switch 415 serving the legacy systems 110, 120, 130), TCP/IP address of the user, profile of the computer system 200 or other communications device associated with the incoming electronic healthcare communication (e.g., presentation formats for various communications devices), a time or date identifier (e.g., day of week or calendar date), other information associated with the electronic healthcare communications signal, size and content of electronic healthcare communication (including types of files that are transmitted as an attached file), transaction reply(s), transaction notification(s), display of a GUI (e.g., color, font, placement of VPO Management Module 210 on screen, etc.), associations with network-based applications, VPO Management Service defaults (e.g., whether the IDS automatically re-formats the attached file to a compatible data format and updates the legacy system with the compatible data format), and other selections related to VPO Management Services, such as electronic healthcare communication features, electronic healthcare communication routing, and troubleshooting problems or error messages.

FIG. 6 illustrates an embodiment of establishing a physicians' office legacy VPO Rule-Based Profile 600 to interact with the VPO Rule-Based Profile 500 of the communications network 210. The VPO Management Module 210 of computer system 200 is used to establish, store, and manage the legacy VPO Rule-Based Profile 600 for legacy system 110 (i.e., the hospital's legacy system). The legacy system 110 stores one or more of the VPO Rule-Based Profiles 600 that include data and applications similar to VPO Rule-Based Profile 500. The legacy VPO Rule-Based Profiles 600, however, provide increased security by allowing the physicians' office 110 to internally control electronic healthcare data and/or communications, utilize existing databases to add, delete, or otherwise change electronic healthcare data and/or communications, control how the physicians' office legacy system 110 (or home legacy system 120) interacts with the practice management application 430 and/or IDS 440, and control routing instructions within its legacy system 110.

FIGS. 7-8 are schematics showing a variety of wired and wireless communications devices communicating the electronic healthcare communication 410 through the communications network 150 according to alternate embodiments of this invention. The means of coupling the computer system 200 or other communications devices (shown as reference numerals 702-718) to switch 415 includes optical transmission of electronic healthcare data, wireless transmission of electronic healthcare data, and/or fixed-wire transmission of electronic healthcare data (e.g., via a local loop of a telecommunications network to communicate electronic healthcare data). Fiber optic technologies, spectrum multiplexing (such as Dense Wave Division Multiplexing), Ethernet and Gigabit Ethernet services, and Digital Subscriber Lines (DSL), and copper conductors are just some examples of the coupling means.

FIG. 7 illustrates a VPO 700 similar to the VPO 300 of FIG. 3. VPO 700, however, illustrates specific communications devices that may be used by the participant 130 (or, alternatively physicians' office 110 and/or home 120 although not shown) and/or the non-participant 140. VPO 700 includes alternate communications devices that include a personal digital assistant (PDA) 702, a mobile phone 704 (e.g., cellular, satellite, Internet Protocol), a modem 706, an interactive pager 708, a global positioning system (GPS) transceiver 710, an MP3 player 712, a digital signal processor (DSP) 714, and an interactive television 716. These alternate communications devices communicate via an antenna 720 communicating with an MTSO 730 that communicates the electronic healthcare communication 410 to the switch 415. Whether the communications devices or the computer system 200 is used, switch 415 routes the electronic healthcare communication 410 to the communications network 150. In addition, FIG. 7 illustrates that the computer system of the physicians' office legacy system 110 includes a variety of communications devices including computer system 200 and wireless communications device, such as PDA 702 (as well as other wireless communications devices, such as reference numerals 704-716). Regardless of the communications device used to send the electronic healthcare communication 410, the electronic healthcare communication 410 may need to be formatted accordingly for the receiving communications device (including audio, text (e.g., ASCII), video, other digital formats, and combination thereof). Thus, the VPO Rule-Based Application DataServer 420 has the intelligence to associate the presentation capabilities of the alternate communications device (associated with participants and non-participants).

FIG. 8 illustrates a VPO 800 similar to the VPO 700 disclosed in FIG. 7. This VPO 800, however, includes a communications device gateway 810 connected with a data network 820 and a communications server 830 so that the electronic healthcare communication 410 communicated to/from switch 415 may be appropriately formatted for presentation on alternate communications devices (such as those shown and described with reference numerals 702-716). For example, if the alternate communications device uses the Wireless Application Protocol (WAP) technique, then the electronic healthcare communication (including transaction replies and/or notifications) 410 is communicated to the communications ("Comm") server 830. The electronic healthcare communications server 830 formats the electronic healthcare communication 410 into one or more Wireless Mark-up Language (WML) messages that are communicated over the data network 820 to the communications device gateway 810. The communications device gateway 810 then interfaces with the MTSO 730, and the MTSO 730 then wirelessly communicates the electronic healthcare communication 410 to the communications devices. The Wireless Mark-up Language (WML) and the WAP technique are known and will not be further described. This is a description of a solution for a specific wireless protocol, such as WAP. This solution may be clearly extended to other wireless protocol, such as i-mode, VoiceXML (Voice eXtensible Markup Language), and other signaling means.

Figure 9:
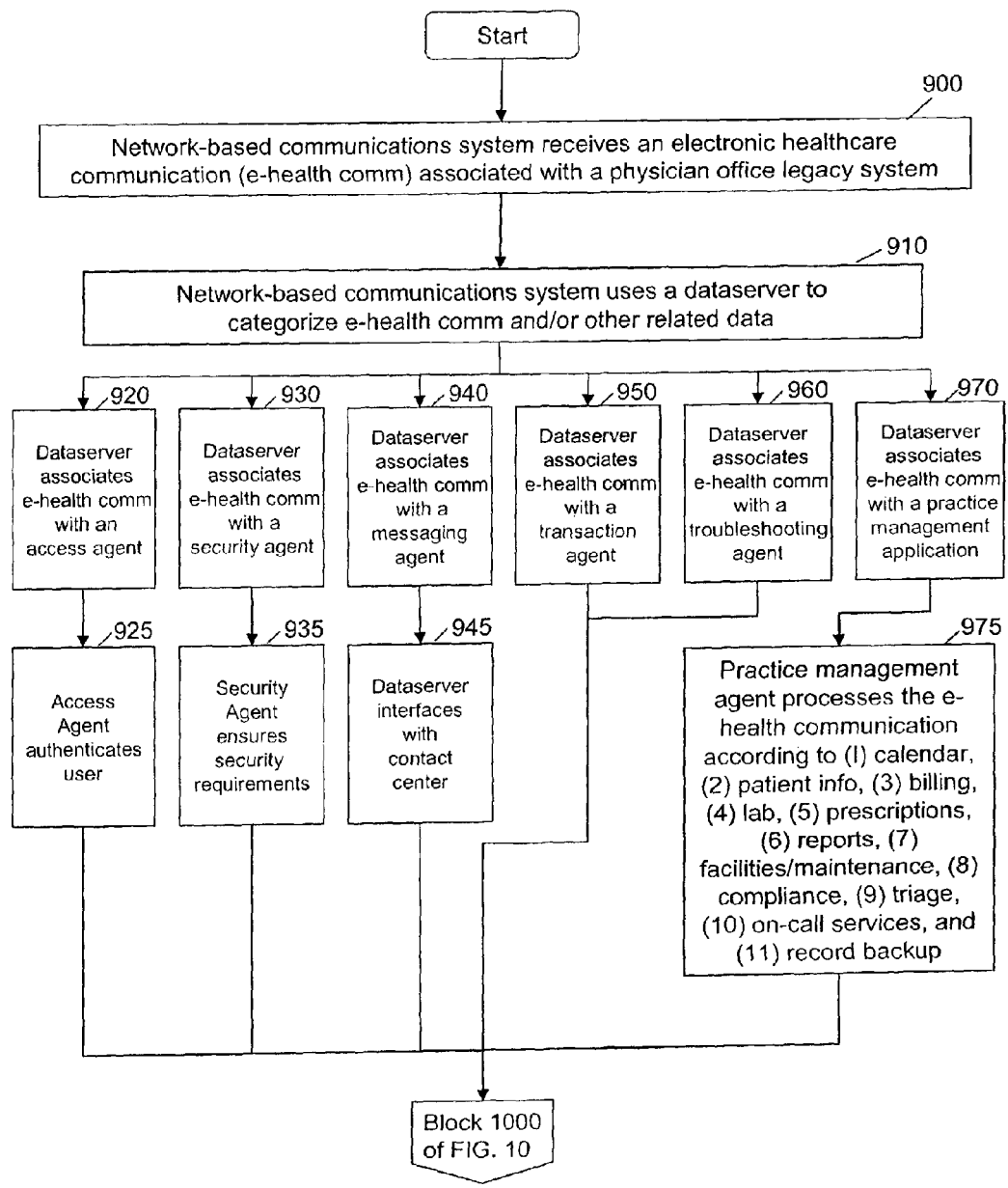
FIGS. 9-11 are flowcharts showing a method of providing VPO services according to an embodiment of this invention.
Figure 10:
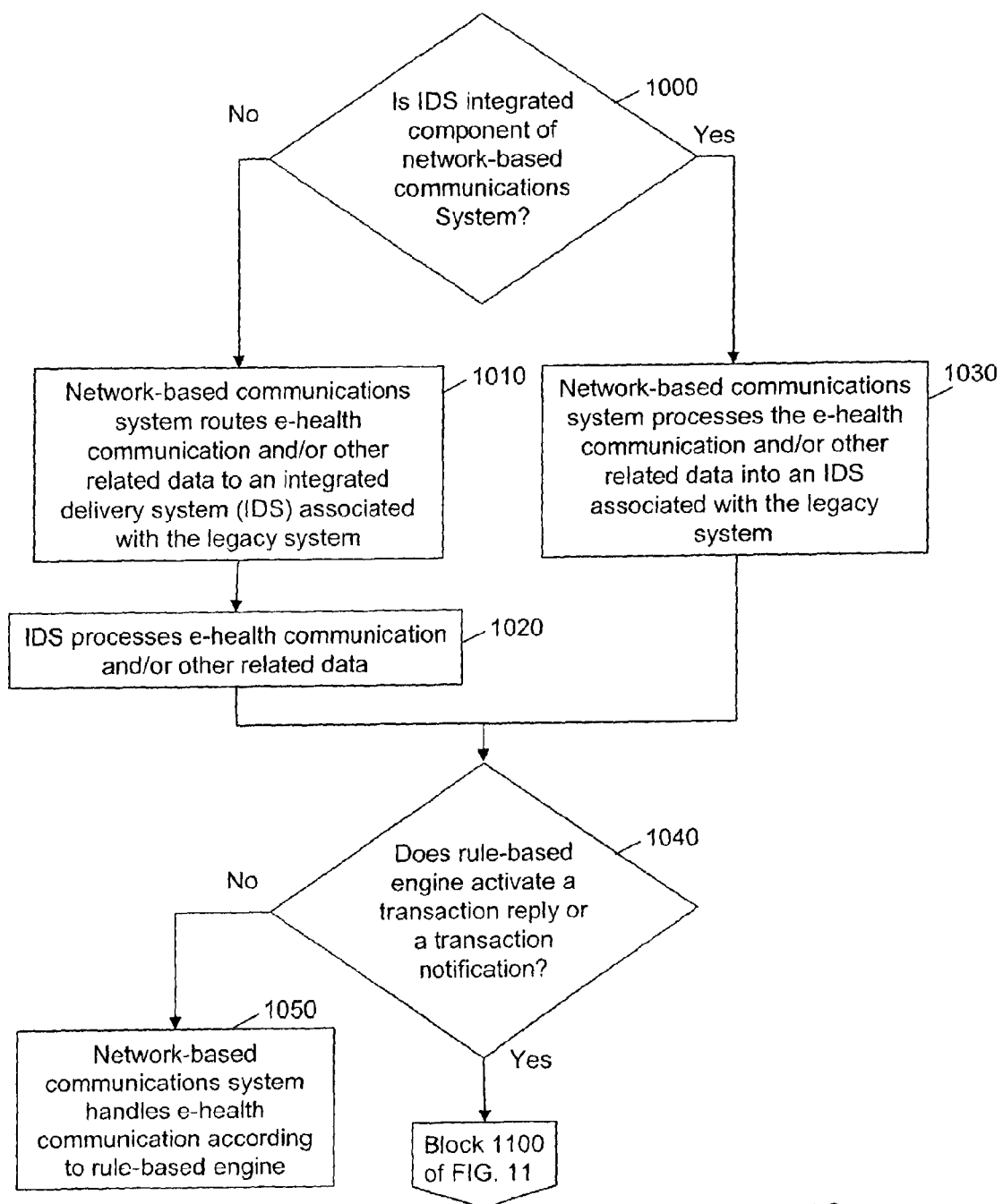
Figure 11:
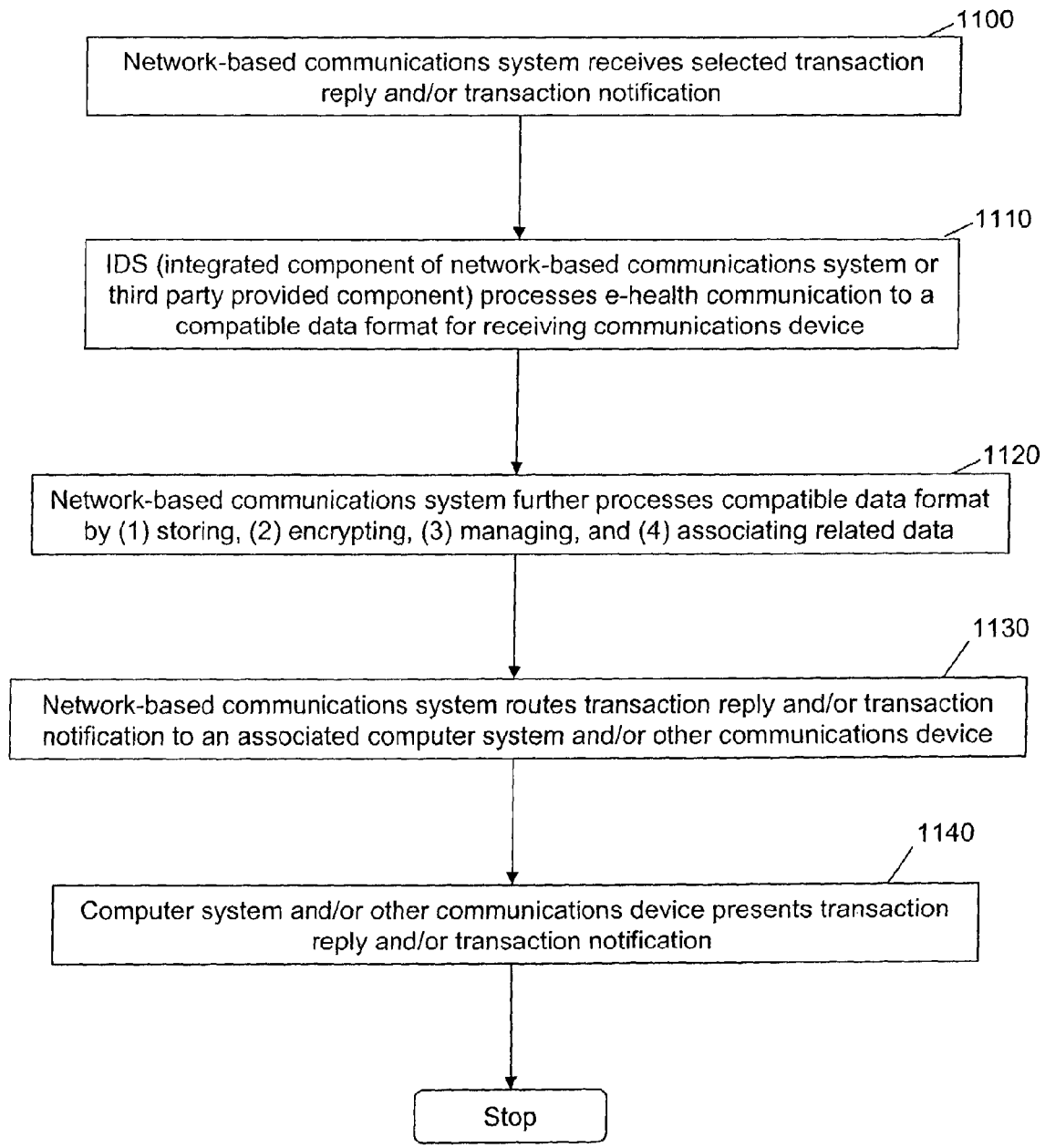

FIGS. 9-11 are flowcharts showing a process of providing the virtual physician office (VPO) services according to an embodiment of this invention. While the process in FIGS. 9-11 is shown in series, these processes may occur in different orders and/or at simultaneous times as one of ordinary skill in the art will understand.

Referring now to FIG. 9, a network-based communications system receives an electronic healthcare communication ("e-health comm") associated with a physician office legacy system (block 900). The network-based communications system categorizes the electronic healthcare communication using a rule-based application dataserver to categorize and associate rule based agents, fields, and/or files (block 910). Accordingly, the dataserver may associate the electronic healthcare communication with an access agent (block 920), a security agent (block 930), a messaging agent (block 940), a transactional agent (block 950), a troubleshooting agent (block 960), and an application agent (970) (e.g., a practice management agent for providing physician office management services). Thereafter, the access agent authenticates the user (block 925). The security agent ensures security requirements associated with the physician office legacy system, home system, other legacy systems, and communications devices of non-participants (block 935). The messaging agent may interface with a contact center, such as for example, the dynamic contact center disclosed in applicants' co-pending U.S. patent application Ser. No. 10/335,113 entitled "Computer Telephony Integration (CTI) Complete Customer Contact Center," filed Dec. 31, 2002 (block 945). The troubleshooting agent provides online help and support as well as contact (via electronic correspondence, voice, and/or video) with customer relations and technical support staff (not shown). The application agent accesses and uses the physician management application to manage at least one of the following: (i) a calendar and schedule, (ii) patient information, (iii) charges and fees, (iv) receipts, (v) laboratory testing, (vi) prescriptions, (vii) reports, (viii) office facilities and maintenance, (ix) compliance and inspections, (x) patient triage and medical protocols, (xi) on-call services, (xii) insurance appeals, (xiii) patient billing, and (xiv) back-up storage settings (block 975).

The flowchart continues with FIG. 10. The method determines whether an integrated delivery system (IDS) is a component of the network-based communications system. If "no," then the network-based communications system routes the electronic healthcare communication to the IDS of a legacy system (block 1010) and the IDS processes the electronic healthcare communication (block 1020). If the IDS is a component of the network-based communications system, then the network based communications system processes the electronic healthcare communication (block 1030). Thereafter, a rule-based engine associated with the dataserver determines whether to activate a transaction reply and/or transaction notification (block 1040). If "no," then the electronic healthcare communication is processed according to the rule-based engine (block 1050). However, if the transaction reply and/or notification is activated (block 1040), then the method continues with FIG. 11. The network-based communications system receives the transaction reply and/or notification (block 1100). The IDS then processes the electronic healthcare data to a compatible data format for the receiving communication (e.g., computer system 200 of physicians' office legacy system 110) (block 1110). Thereafter, the network-based communications system may further process the compatible data format by sorting, encrypting, managing, and/or associating other related data (block 1120). Next, the transaction replay and/or notification is routed to an associated computer system and/or communications device (block 1130). Finally, the computer system and/or communications device presents the transaction reply and/or notification (block 1140).

While several exemplary implementations of embodiments of this invention are described herein, various modifications and alternate embodiments will occur to those of ordinary skill in the art. Accordingly, this invention is intended to include those other variations, modifications, and alternate embodiments that adhere to the spirit and scope of this invention.

The invention claimed is:

1. A method, comprising:
   receiving, at a server, an electronic healthcare message formatted in a legacy format for a device identified by a recipient address;
   comparing, by the server, the recipient address to a list of addresses;
   determining, by the server, a match between the recipient address and an entry in the list of addresses;
   reformatting, by the server, the electronic healthcare message from the legacy format into a reformatted healthcare message that is compatible with a different format associated with the recipient address; and
   sending, from the server, the reformatted healthcare message to the recipient address.

2. The method of claim 1, further comprising executing a rule associated with the recipient address.

3. The method of claim 1, further comprising executing a rule associated with the different format.

4. The method of claim 1, further comprising categorizing the electronic healthcare message.

5. The method of claim 1, further comprising associating the legacy format to a software agent that reformats the electronic healthcare message.

6. The method of claim 1, further comprising encrypting the reformatted healthcare message.

7. The method of claim 1, further comprising associating the recipient address with a profile.

8. A system, comprising:
a processor; and
a memory storing code that when executed causes the processor to perform operations, the operations comprising:
receiving an electronic healthcare message formatted in a legacy format for a device identified by a recipient address;
comparing the recipient address to a list of addresses;
determining a match between the recipient address and an entry in the list of addresses;
reformatting the electronic healthcare message from the legacy format into a reformatted healthcare message that is compatible with a different format associated with the recipient address; and
sending the reformatted healthcare message to the recipient address.

9. The system of claim 8, wherein the operations further comprise executing a rule associated with the recipient address.

10. The system of claim 8, wherein the operations further comprise executing a rule associated with the different format.

11. The system of claim 8, wherein the operations further comprise categorizing the electronic healthcare message.

12. The system of claim 8, wherein the operations further comprise associating the legacy format to a software agent that reformats the electronic healthcare message.

13. The system of claim 8, wherein the operations further comprise encrypting the reformatted healthcare message.

14. The system of claim 8, wherein the operations further comprise associating the recipient address with a profile.

15. A memory storing code that when executed causes a processor to perform operations, the operations comprising:
receiving an electronic healthcare message formatted in a legacy format and destined for delivery to device identified by a recipient address;
comparing the recipient address to a list of addresses;
determining a match between the recipient address and an address in the list of addresses;
reformatting the electronic healthcare message from the legacy format into a reformatted healthcare message that is compatible with a different format associated with the recipient address; and
sending the reformatted healthcare message to the recipient address.

16. The memory of claim 15, wherein the operations further comprise executing a rule associated with the recipient address.

17. The memory of claim 15, wherein the operations further comprise executing a rule associated with the different format.

18. The memory of claim 15, wherein the operations further comprise categorizing the electronic healthcare message.

19. The memory of claim 15, wherein the operations further comprise associating the legacy format to a software agent that reformats the electronic healthcare message.

20. The memory of claim 15, wherein the operations further comprise encrypting the reformatted healthcare message.

* * * * *